(12) United States Patent
Cappelletti (10) Patent No.: US 10,022,229 B2
(45) Date of Patent: Jul. 17, 2018

(54) ADJUSTABLE MODULAR SPACER DEVICE FOR THE ARTICULATIONS OF THE HUMAN BODY

(71) Applicant: Ava Cappelletti, Cesena (IT)

(72) Inventor: Ava Cappelletti, Cesena (IT)

(73) Assignee: COSSINGTON LIMITED, Kingston Upon Thames, Surrey (GB)

( * ) Notice: Subject to any disclaimer, the term of this patent is extended or adjusted under 35 U.S.C. 154(b) by 0 days.

(21) Appl. No.: 14/917,155

(22) PCT Filed: Sep. 9, 2013

(86) PCT No.: PCT/IT2013/000236
§ 371 (c)(1),
(2) Date: Mar. 7, 2016

(87) PCT Pub. No.: WO2015/033362
PCT Pub. Date: Mar. 12, 2015

(65) Prior Publication Data
US 2016/0193050 A1    Jul. 7, 2016

(51) Int. Cl.
*A61F 2/30* (2006.01)
*A61F 2/36* (2006.01)
*A61F 2/40* (2006.01)

(52) U.S. Cl.
CPC ............. *A61F 2/30* (2013.01); *A61F 2/3609* (2013.01); *A61F 2/4014* (2013.01);
(Continued)

(58) Field of Classification Search
CPC ...... A61F 2002/2825; A61F 2002/2828; A61F 2002/2853; A61F 2002/2832; A61F 2/32;
(Continued)

(56) References Cited

U.S. PATENT DOCUMENTS 4,822,370 A * 4/1989 Schelhas .............. A61F 2/3609
                                                    623/22.46
5,358,526 A * 10/1994 Tornier ................. A61F 2/4059
                                                    623/19.14
(Continued)

FOREIGN PATENT DOCUMENTS

WO      96/17553      6/1996
WO   2005/089676      9/2005
(Continued)

*Primary Examiner* — Alvin Stewart
(74) *Attorney, Agent, or Firm* — Duane Morris LLP; Gregory M. Lefkowitz; Jason M. Nolan (57) ABSTRACT

An adjustable spacer modular device for the treatment of an articulation of the human body, comprising a fitting central body provided with an end having a substantially flat first surface, a head adapted to be arranged within an articular cavity, wherein the head comprising a cap and a base opposite to said cap, wherein the cap and the base are radiused to each other, a rod-like element, adapted to be fixedly connected at a bone end, first means for connecting the head to the central body, wherein the first connection means are adjustable and adapted to adjust the inclination of the head with respect to the central body along a longitudinal plane and/or along a transverse plane of the human body.

19 Claims, 4 Drawing Sheets

(52) U.S. Cl.
CPC ........... *A61F 2/30734* (2013.01); *A61F 2/367* (2013.01); *A61F 2002/305* (2013.01); *A61F 2002/3054* (2013.01); *A61F 2002/3055* (2013.01); *A61F 2002/3092* (2013.01); *A61F 2002/30332* (2013.01); *A61F 2002/30405* (2013.01); *A61F 2002/30426* (2013.01); *A61F 2002/30449* (2013.01); *A61F 2002/30538* (2013.01); *A61F 2002/30604* (2013.01); *A61F 2002/30616* (2013.01); *A61F 2002/30617* (2013.01); *A61F 2002/30672* (2013.01); *A61F 2002/30677* (2013.01); *A61F 2002/365* (2013.01); *A61F 2002/3647* (2013.01); *A61F 2002/3652* (2013.01); *A61F 2002/3674* (2013.01); *A61F 2002/4029* (2013.01); *A61F 2002/4037* (2013.01); *A61F 2002/4044* (2013.01); *A61F 2250/006* (2013.01); *A61F 2310/00353* (2013.01); *A61F 2310/00952* (2013.01)

(58) Field of Classification Search
CPC .. A61F 2/30; A61F 2/36; A61F 2/3609; A61F 2002/3615; A61F 2002/3625; A61F 2002/365; A61F 2002/3662; A61F 2002/3654; A61F 2002/3656
USPC ....................... 623/22.42–22.46, 23.11, 23.15
See application file for complete search history.

(56) References Cited

U.S. PATENT DOCUMENTS

| | | | | |
|---|---|---|---|---|
| 5,507,818 A * | 4/1996 | McLaughlin | A61F 2/32 | 623/23.42 |
| 5,580,352 A * | 12/1996 | Sekel | A61F 2/36 | 606/62 |
| 6,200,350 B1 * | 3/2001 | Masini | A61F 2/36 | 623/23.15 |
| 6,238,436 B1 * | 5/2001 | Lob | A61F 2/367 | 623/22.42 |
| 6,383,225 B2 * | 5/2002 | Masini | A61F 2/36 | 623/22.42 |
| 6,440,171 B1 * | 8/2002 | Doubler | A61F 2/36 | 623/22.42 |
| 6,520,994 B2 * | 2/2003 | Nogarin | A61F 2/30771 | 623/19.14 |
| 6,702,854 B1 * | 3/2004 | Cheal | A61F 2/36 | 623/22.42 |
| 6,719,799 B1 * | 4/2004 | Kropf | A61F 2/4014 | 623/19.12 |
| 6,749,637 B1 * | 6/2004 | Bahler | A61F 2/4014 | 623/19.11 |
| 7,070,622 B1 * | 7/2006 | Brown | A61F 2/36 | 623/20.14 |
| 7,108,719 B2 * | 9/2006 | Horber | A61F 2/4014 | 623/18.11 |
| 7,306,629 B2 * | 12/2007 | Saladino | A61F 2/3609 | 623/22.42 |
| 7,458,989 B2 * | 12/2008 | Banks | A61B 5/6846 | 600/300 |
| 7,491,242 B2 * | 2/2009 | Pichon | A61F 2/30734 | 623/23.21 |
| 7,985,261 B2 * | 7/2011 | Masini | A61F 2/36 | 623/22.21 |
| 7,998,217 B1 * | 8/2011 | Brown | A61F 2/3609 | 623/20.14 |
| 8,052,758 B1 * | 11/2011 | Winslow | A61F 2/4014 | 623/22.42 |
| 8,128,705 B2 * | 3/2012 | Birkbeck | A61F 2/4637 | 623/23.11 |
| 8,303,665 B2 * | 11/2012 | Tornier | A61F 2/4081 | 623/19.11 |
| 8,425,618 B2 * | 4/2013 | Caillouette | A61F 2/36 | 623/22.42 |
| 8,533,968 B2 * | 9/2013 | Anapliotis | A61F 2/30721 | 33/1 BB |
| 8,562,690 B1 * | 10/2013 | Dickerson | A61F 2/367 | 623/22.42 |
| 8,702,804 B2 * | 4/2014 | Smith | A61F 2/4014 | 623/19.11 |
| 8,795,379 B2 * | 8/2014 | Smith | A61F 2/3609 | 623/19.14 |
| 8,840,676 B2 * | 9/2014 | Belew | A61F 2/4684 | 623/22.15 |
| 8,906,103 B2 * | 12/2014 | Stone | A61F 2/4014 | 623/19.11 |
| 9,326,862 B2 * | 5/2016 | Smith | A61F 2/3859 | |
| 9,345,580 B2 * | 5/2016 | Porter | A61F 2/0811 | |
| 9,427,322 B1 * | 8/2016 | Serafin, Jr. | A61F 2/3662 | |
| 9,504,580 B2 * | 11/2016 | Link | A61F 2/367 | |
| 2001/0008981 A1 * | 7/2001 | Masini | A61F 2/36 | 623/22.42 |
| 2001/0053935 A1 * | 12/2001 | Hartdegen | A61F 2/4684 | 623/19.12 |
| 2003/0028253 A1 * | 2/2003 | Stone | A61F 2/4014 | 623/19.14 |
| 2003/0074078 A1 * | 4/2003 | Doubler | A61F 2/36 | 623/22.42 |
| 2003/0074080 A1 * | 4/2003 | Murray | A61F 2/3609 | 623/22.42 |
| 2003/0088316 A1 * | 5/2003 | Ganjianpour | A61F 2/3609 | 623/22.42 |
| 2005/0043811 A1 * | 2/2005 | Doubler | A61F 2/36 | 623/22.42 |
| 2006/0142872 A1 * | 6/2006 | Klotz | A61F 2/4014 | 623/23.44 |
| 2007/0198094 A1 * | 8/2007 | Berelsman | A61F 2/4014 | 623/19.14 |
| 2007/0219641 A1 * | 9/2007 | Dorr | A61F 2/30767 | 623/22.42 |
| 2008/0140210 A1 | 6/2008 | Doubler et al. | | |
| 2008/0140211 A1 * | 6/2008 | Doubler | A61F 2/4014 | 623/19.14 |
| 2010/0114324 A1 * | 5/2010 | Gibbs | A61F 2/30739 | 623/22.42 |
| 2010/0152860 A1 * | 6/2010 | Brooks | A61F 2/4637 | 623/22.42 |
| 2010/0241239 A1 * | 9/2010 | Smith | A61B 17/1668 | 623/22.42 |
| 2010/0249943 A1 * | 9/2010 | Bergin | A61F 2/3609 | 623/22.42 |
| 2011/0035013 A1 * | 2/2011 | Winslow | A61F 2/4003 | 623/19.13 |
| 2011/0247229 A1 * | 10/2011 | Anapliotis | A61F 2/30721 | 33/512 |
| 2012/0010720 A1 * | 1/2012 | Dickerson | A61F 2/30734 | 623/22.42 |
| 2012/0035733 A1 * | 2/2012 | Porter | A61F 2/0811 | 623/18.11 |
| 2013/0211535 A1 * | 8/2013 | Cueille | A61F 2/3609 | 623/22.44 |
| 2013/0245782 A1 * | 9/2013 | Anapliotis | A61F 2/32 | 623/23.4 |
| 2014/0172115 A1 * | 6/2014 | Porter | A61F 2/30739 | 623/23.15 |
| 2015/0257888 A1 * | 9/2015 | Acker | A61F 2/30767 | 623/23.18 |
| 2016/0262912 A1 * | 9/2016 | Burnikel | A61F 2/4684 | |

FOREIGN PATENT DOCUMENTS

WO 2012/125795 9/2012
WO 2013/041906 3/2013

* cited by examiner

ADJUSTABLE MODULAR SPACER DEVICE FOR THE ARTICULATIONS OF THE HUMAN BODY

CROSS-REFERENCE TO RELATED APPLICATIONS

This application is a § 371 national stage entry of International Application No. PCT/IT2013/000236, filed Sep. 9, 2013, the entire content of which is incorporated herein by reference.

TECHNICAL FIELD OF THE INVENTION

The present invention regards a disposable temporary spacer device of the modular adjustable type for the articulation of the human body, particularly suitable for the technique referred to as "two-stage implant" of a spacer for the hip and/or shoulder articulation. In particular, such device is used with support and treatment functions in case of a two-stage revision of the infected prosthesis of the hip and/or of the shoulder. Such device allows for maintaining the space required by the implant of a new prosthesis and guaranteeing a high mobility of the articulation.

PRIOR ART

In the field of prosthesis implantology, temporary spacer devices used, in particular, in the technique referred to as "two-stage implant", are known. Such know technique provides, in case of infection of an articular prosthesis, for the removal thereof to allow for treating the articular seat with suitable medicinal substances. Moreover, in order to maintain the space required for the implant of a new prosthesis, within the articular seat, the use of spacer devices is provided. In particular, such spacer devices can be impregnated with medicinal substances and serve a double function: maintaining the articular space required for the implant of a new prosthesis and treating the infection site.

With reference to the shoulder articulation, the spacer devices comprise a first portion, or body, to be fixedly connected to the upper end of the humerus and a second portion, or head, to be positioned at the glenoid cavity.

With reference to the hip articulation, the spacer devices comprise a first portion, or body, to be fixedly connected to the upper end of the femur and a second portion, or head, to be positioned at the acetabular cavity.

The International patent application WO2010/015877, on behalf of the applicant, describes a hip spacer device.

Such spacer device comprises connection means, between the first portion and the second portion, adapted to modify the relative position of such portions and, thus, capable of being adapted to articular cavities of different dimensions.

However, there arises the need of providing a greater capacity of adapting the dimensions of the spacer device to different sizes of the articular seat (acetabulum and/or glenoid), in which the same is applied, with the aim of guaranteeing a greater compatibility and congruence of the device with the different dimensions of the articulations of the patients, also in presence of serious diseases. In this way, a better life quality of the patient during the period required for treating the infection present in the seat of the articulation is guaranteed.

DISCLOSURE OF INVENTION

An object of the present invention is to improve the state of the prior art.

A further object of the present invention is that of providing an adjustable temporary spacer device which can be easily adaptable to different and actual anatomic dimensions of the articulation in which it is applied, determined by the removal of the infected articular prosthesis.

A further object of the present invention is that of proposing an adjustable temporary modular spacer device for the hip and/or shoulder articulation capable of guaranteeing a high mobility and stability of the articulation and, thus, a good life quality to the patient during the period of rehabilitation following the implantation of the device.

According to an aspect of the present invention a temporary spacer device of the hip and/or of the shoulder according to claim 1 is provided.

The dependent claims refer to preferred and advantageous embodiments of the invention.

BRIEF DESCRIPTION OF DRAWINGS

Further characteristics and advantages of the present invention will be more apparent from the detailed description of a preferred but non-exclusive embodiment of a modular adjustable temporary spacer device for the hip and/or shoulder articulation, illustrated by way of non-limiting example, in the attached drawings wherein.

EMBODIMENTS OF THE INVENTION

With reference to the embodiment illustrated in the attached figures, an adjustable temporary modular spacer device for the hip articulation is indicated with 1.

The present invention may also be intended for the realization of an adjustable temporary modular spacer for the articulation of a shoulder, without departing from the scope of protection of the present invention.

For the sake of clarity, the modular adjustable temporary spacer device for the hip and/or shoulder articulation will be indicated hereinafter as "spacer device".

Figures 1, 2:
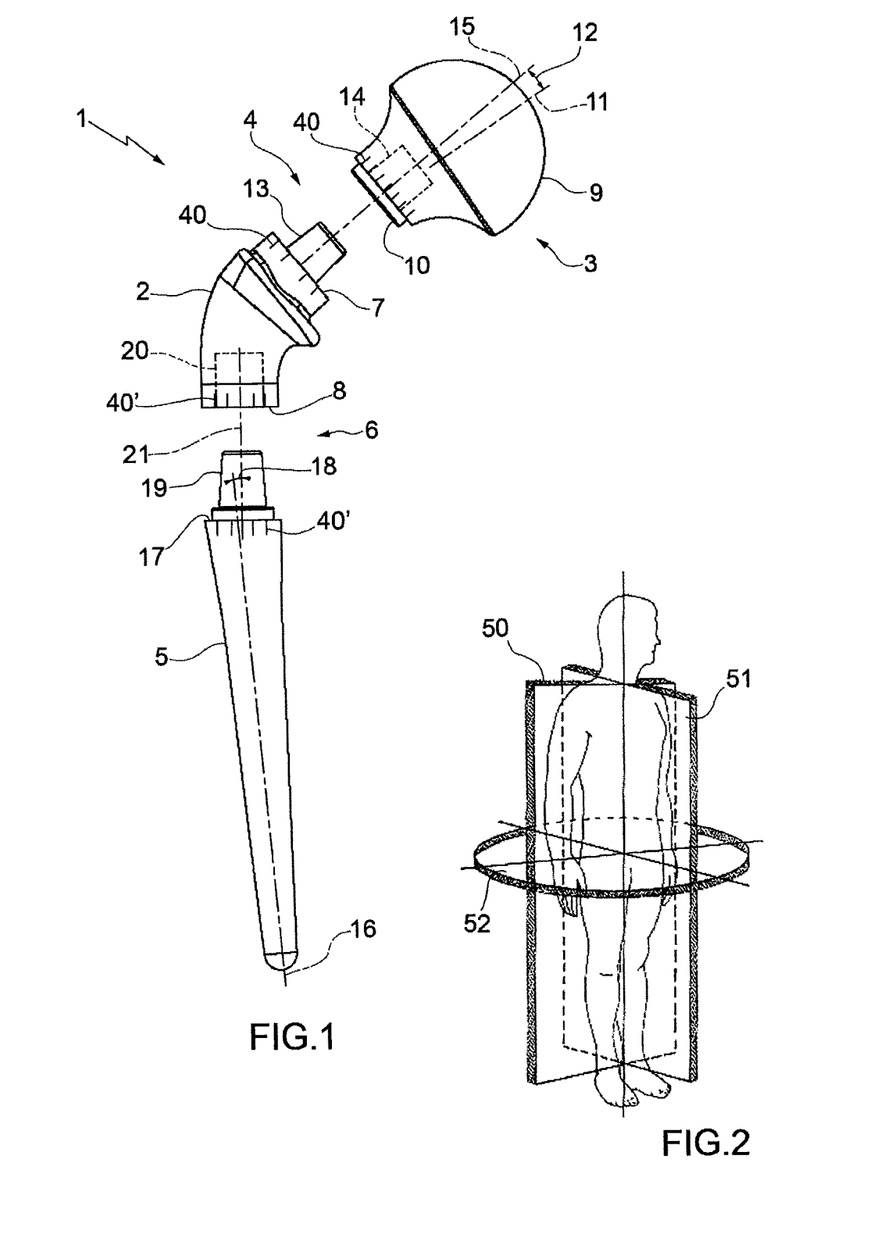
FIG. 1 is an exploded side view of an adjustable modular spacer device according to the invention.
FIG. 2 is a perspective scheme of the symmetry planes of the human body

The FIG. 2 shows the symmetry planes of the human body. In particular, the expression "longitudinal plane" shall be used to indicate the vertical symmetry plane 50 of the human body, passing through the joining line of the shoulders; the expression "sagittal plane" is used to indicate the bilateral symmetry vertical plane 51 of the human body, passing through the median line of the human body, which identifies a right portion and a left portion; the expression "transverse plane" is used to indicate a horizontal plane 52 which identifies—in the human body—an upper portion and a lower portion.

In an upright position such transverse plane is horizontal. Furthermore, such transverse plane is perpendicular to the longitudinal plane 50 and to the sagittal plane 51 previously described.

The spacer device 1 according to the present invention is of the disposable type.

The spacer device 1, according to the present invention, comprises a central body 2, a head 3, adapted to be arranged in the acetabular cavity of the articulation of the hip or in the glenoid cavity of the shoulder articulation, first means 4 for connecting the central body 2 to the head 3, a rod-like element 5, adapted to be fixedly connected at a bone end of the articulation of the hip, or at the upper end of the humerus, or at the bone end of the knee articulation, or at the upper end of the femur, or at the central body 2.

The central body 2, the head 3 and the rod-like element 5 are assembled together to constitute the spacer device 1 according to the present invention.

The central body 2, that acts has a connecting element between the head 3 and the rod-like element 4, may present a substantially "elbow" shape.

However, other further versions of the central body 2 characterized by a curvature greater or lesser that the previous one or by a different shape, for example by a "L-shape" or similar, etc, are possible.

At the opposite ends of the central body 2 a first surface 7 and a second surface 8, both substantially flat, are provided.

In particular, following the assembling of the spacer device 1, the first surface 7 is in abutment against the head 3, while the second surface 8 is placed in abutment against the rod-like element 5, has better described hereinafter.

The head 3 comprises, at one end, a spherical or semispherical or similarly-shaped cap 9, suitable to be positioned within the glenoid or acetabular articular cavity, and at the opposite end a base 10.

During the coupling of the first connection means 4, the first surface 7 of the central body 2 is abutted against the base 10 of the head 3.

The cap 9, that is radiused to the base 10, has a central symmetry axis 11.

The base 10 may be perpendicular or inclined with respect to the central symmetry axis 11 of the cap 9. The first connection means 4, that are positioned between the central body 2 and the head 3, comprise a pin 13 and a corresponding seat 14.

In the version shown in FIG. 1, the pin 13 projects from the end 7 of the central body 2 while the seat 14 is provided in the head 3, at the base 10 thereof. According to a further embodiment, the position of the pin 13 and that of the seat 14 can be inverted each other. Therefore, with reference to the embodiment shown in FIG. 6, the pin 13' departs from the base 10 of the head 3 while the seat 14' is obtained in the central body 2, at the first surface 7 thereof.

During the step of assembling the head 3 to the central body 2, the pin 13 is inserted within the seat 14.

The pin 13 and the seat 14 are complementary with respect to each other and identify a first longitudinal coupling axis 15.

With reference to the embodiment shown in FIG. 1, wherein the spacer device 1 is in the longitudinal plane 50, the first axis 15, of the first connection means 4, is inclined with respect to the direction of the central symmetry axis 11 of the cap 9 by an angle 12.

The inclination of the first axis 15 with respect to the central symmetry axis 11 allows for providing different configurations of assembly of the spacer device 1, thus causing different inclinations of the head 3 with respect to the central body 2 as better indicated hereinafter.

The width of the angle 12 may be comprised in a range between 5° and 20°.

Preferably, the width of the angle 12 is comprised in a range between 5° and 12°.

During the step of assembling of the first connection means 4, the base 10 of the head 3 is perpendicular to the first axis 15. Therefore, also the base 10 is inclined by an angle equal to the angle 12 with respect to the central symmetry axis 11 of the cap 9. In particular, the first connection means 4, during the step of assembling, allow the relative rotation of the head 3 with respect to the central body 2, around the first axis 15, allowing to realize different configurations of assembly, as better described hereinafter.

During the connection of the first connection means 4, a precession motion of the spherical cap 9 around the first axis 15 is determined, by turning the central head 3 around the first axis 15.

Indeed, as previously disclosed, the central symmetry axis 11 of the spherical cap 9 is inclined with respect to the first axis 15 of the first connection means 4.

Therefore, by turning the head 3 around the first axis 15 the inclination of the head 3 with respect to the central body 2 is modified along the frontal plane 30 and or the transverse plane 52.

In order to allow the surgeon to obtain the desired assembly configuration, with reference to the relative orientation of the head 3 with respect to the central body 2, reference notches 40 can be provided on the head 3, at the base 10, and/or on the central body 2 at the surface 7.

When the desired assembly configuration between the head 3 and the central body 2 is reached, the pin 13 is held within the seat 14 through a bonding agent, for example bone cement or generally a substance that is compatible with the purpose the spacer device 1 is intended for or with the material thereof, or through mechanical and/or snap-coupling connection means or other similar means.

By way of example, in a version not indicated in the figures, the pin 13 has an external threading. Analogously, the seat 14 has an internal threading matching the external threading of the pin 13.

In such version, the pin 13 is connected to the seat according to the indications below. First and foremost, a suitable amount of bonding agent is inserted into the seat 14. Subsequently, the pin 13 is screwed within the seat 14, possibly up to the end stop. The curing of the bonding agent allows for preventing the relative rotation between the pin 13 and the seat 14 thus preventing loosening or relative movements between the head 3 and the central body 2 that could reduce the efficiency of the spacer device 1.

In a further version of the spacer device 1, not indicated in the attached figures, the first connection means 4 may comprise quick coupling means, for example snap-coupling means or of the bayonet type or of the morse-taper type or similar connections, which, after being correctly positioned in the desired configuration of assembly, can be mutually fixedly connected to each other by using a bonding agent.

Such bonding agent prevents relative rotations or movements between the head 3 and the central body 2 which could reduce the stability and the efficiency of the spacer device 1 in use. With reference to the embodiment shown in FIG. 1, the rod-like element 5 has an elongated shape, substantially a frusto-conical shape, suitable to be place into the upper end of the humerus or of the femur.

Such configuration of the rod-like element 5 allows to obtain a stable connection of the spacer device 1 within the bone end of the humerus or the bone end of the femur even in presence of specific and significant resections of the bone end.

The rod-like element 5 can be fixedly connected to the bone ends of the patient by using bone cement or substances suitable to guarantee a stable connection thereof.

In a version of the invention, the rod-like element 5 has a longitudinal axis 16 and, at the end opposite to that one suitable to be inserted into the bone end, a substantially flat base 17.

The base 17 can be perpendicular or inclined with respect to the longitudinal axis 16.

According to such version, the device 1 comprises second connection means 6, suitable to connect to central body 2 to the rod-like element 5.

In particular, the second connection means 6 are placed between the central body 2 and the rod-like element 5.

The second connection means 6, analogously to what has been described previously regarding the first connection means 4, comprise a pin 19 and a seat 20.

In the embodiment shown in FIG. 1, the pin 19 projects from the upper end of the rod-like element 5 while the seat 20 is obtained in the central body 2, at the second surface 8 thereof.

According to a further embodiment, not illustrated, the position of the pin 19 and that of the seat 20 can be inverted each other. Therefore, the pin 19 departs from the second surface 8 of the central body 2 while the seat 20 is obtained in the upper end of the rod-like element 5, at the first base 17.

The type of the second connection means 6, as well as their assembly mode, is similar to that described for the first connection means 4 and, therefore, they will not be further described.

The pin 19 and the seat 20 are complementary to each other and define a second axis 21.

With reference to the embodiment shown in FIG. 1, the second axis 21 is inclined with respect to the longitudinal axis 16 of the rod-like element 5 by an angle 18.

The inclination of the second axis 21, of the second connection means 6, with respect to the longitudinal axis of the rod-like element 5, allows to obtain different configurations of assembly of the spacer device 1, and to vary to inclination of the rod-like element 5 with respect to the central body 2 as better disclosed hereinafter.

The width of the angle 18 can be comprised in a range between 3° and 20°.

Preferably, the width of the angle 18 is comprised in a range between 3° and 10°.

During the connection of the second connection means 6, analogously to what previously described for the first connection means 4, a precession motion of the rod-like element 5 around the second axis 21 is determined, by turning the rod-like element 5 around the second axis 21.

Therefore, by turning the rod-like element 5 around the second axis 21 the inclination of the rod-like element 5 with respect to the central body 2 is modified along the longitudinal plane 50 and/or the sagittal plane 51.

Even in this case, in order to allow the surgeon to locate the relative orientation of the rod-like element 5 with respect to the central body 2, reference notches 40' are provided.

Figure 3:
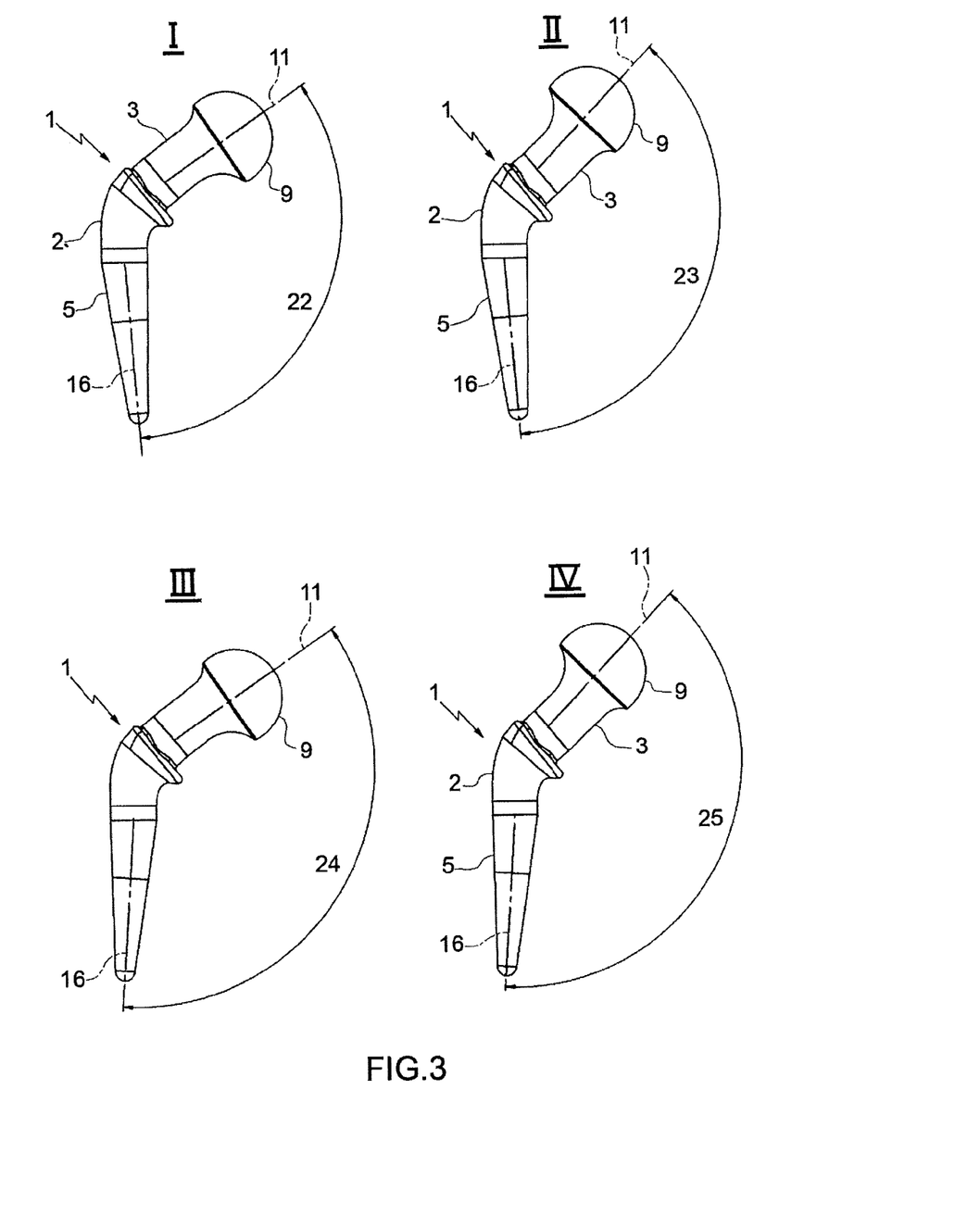
FIG. 3 is a scheme of a some possible configurations of assembly of the adjustable modular spacer device according to the invention.

In particular, the reference notches 40' can be provided at the upper end of the rod-like element 5 and/or of the second surface 8 of the central body 2. In FIG. 3, by way of an non-limitative example, some possible configuration of assembly of the spacer device 1, resting for example on the longitudinal plane 50, are show indicated by references I, II, III and IV.

With reference to the first configuration of assembly I, the central symmetry axis 11, of the cap 9, is inclined with respect to the longitudinal axis 16, of the rod-like element 5, by a first angle 22.

By turning the head 3 with respect to the central body 2, around the first axis 15, of about 180°, the second configuration of assembly II is reached, wherein the central symmetry axis 11 is inclined with respect of the longitudinal axis 16 by a second angle 23.

In particular, the second angle 23 is greater than the first angle 22.

Further, starting from the first configuration of assembly I and turning the rod-like element 5 with respect to the central body 2, around the second axis 21, a third configuration of assembly III is reached. In particular, such configuration of assembly III is obtained by turning the rod-like element 5 of about 180° with respect to the central body 2.

In the third configuration of assembly III the central symmetry axis 11 is inclined with respect of the longitudinal axis 16 by a third angle 24. In particular, the third angle 24 is greater than the first angle 22.

Finally, starting from the third configuration of assembly III and turning the head 3 around the axis 15 of the first connection means 4, of about 180°, the fourth configuration of assembly IV is reached.

In the fourth configuration of assembly IV the cap 9 is inclined with respect to the longitudinal axis 16 of a fourth angle 25, that is greater than the first angle 22, the second angle 23 and the third angle 24. Therefore, with reference to the above, the width of the inclination of the central symmetry axis 9 of the head 3 with respect to the longitudinal axis 16 of the rod-like element 5 shape can be modified. With reference to the longitudinal plane 50, the width of such inclination is comprised in a range between 100° and 160°. Preferably the width of the inclination of the central symmetry axis 9 with respect to the longitudinal axis 16, resting in the longitudinal plane 50, is comprised between 110° and 150°.

Certainly it is possible to obtain a substantially infinite number of configuration of assembly of the spacer device 1, according to the amount of the rotation of the head 3 around the first axis 15 of the first connection means 4 and/or of the rod-like element 5 around the second axis 21 of the second connection means 6.

Therefore, by turning the head 3 with respect to the central body 2, around the first axis 15, a variation of the orientation of the cap 9 with respect to the central body 2 is caused, with respect to the longitudinal plane 50 and/or the transverse plane 52. Similarly, by turning the rod-like element 5 around the second axis 21, the inclination of the rod-like element 5 with respect to the central body 2 is modified along the longitudinal plane 50 and/or the sagittal plane 51.

Therefore, the dimensions of the spacer device 1 can be easily modified, and in particular the relative orientation of the head 3 and/or of the rod-like element 5 with respect to the central body 2, thus adapting the space device 1 to specific dimensions of the shoulder and/or of the knee articulation of the patients, in a practice and quick way, thus reducing the time required for the implant.

The central body 2, the head 3 and the rod-like element 5 are preformed and realized in biologically compatible material.

Such biologically compatible material is porous and it can be selected from among metals, metal alloys, organometallic compounds, ceramics, plastic materials and/or a combination thereof.

Specifically, the aforementioned plastic materials can be selected from among thermoplastic polymers, such as acrylic resins, polyethylene, polypropylene, polyester, etcetera, thermoformable polymers and other similar materials.

In a version of the present invention, the biologically compatible material is a bone cement, for example of the type described in the Italian patent no. 1278853 on behalf of the applicant, incorporated herein for reference.

The aforementioned biologically compatible material, due to the porosity thereof, may be pre-impregnated with pharmaceutical and/or therapeutic products.

In another embodiment, the biologically compatible material, originally without medicinal substances, may be added, possibly by impregnation, with pharmaceutical and/or therapeutic products during the surgical intervention, in the moments prior to the implantation thereof.

In addition, in another embodiment, the biologically compatible material, pre-impregnated with pharmaceutical and/or therapeutic products, may be further added, during the surgical intervention, in the moments prior to the implantation thereof, with pharmaceutical and/or therapeutic products, identical or different from those already contained therein, depending on the needs of the surgeon.

In another embodiment, at least part of the central body 2, and/or of the head 3 and/or of the rod-like element 5 are covered with a padding comprising at least one pharmaceutical and/or therapeutic product. Furthermore, such at least one pharmaceutical and/or therapeutic product may be held in a shell suitable for a slow release thereof over time. Such shell can be made of polymethylmethacrylate and/or a substance suitable for the purpose.

By way of illustrating but non-limiting example, the at least one pharmaceutical and/or therapeutic product comprises Gentamicin and/or Vancomycin and/or Clindamycin and/or other antibiotic substances and/or an anti-infective drug suitable for the purpose and/or a combination thereof.

In particular, the central body 2, the head 3 and the rod-like element 5 comprise the same pharmaceutical and/or therapeutic product.

In a further version, at least two components of the spacer device 1 comprise the same pharmaceutical and/or therapeutic product.

In still another version, the central body 2, the head 3 and the rod-like element 5 comprise pharmaceutical and/or therapeutic products different from each other.

In such case, the various pharmaceutical and/or therapeutic products contained in the various components of the spacer device 1 obtain a synergic effect. The presence of several antibiotics, for example, allows expanding the action spectrum, improving the healing prognosis of the patient.

By way of non-limiting example, a version of the spacer device 1 according to the present invention may comprise the rod-like element 5 filled with a combination of Gentamicin and Vancomycin and the head 3 filled with Gentamicin and Clindamycin.

In a further example, the rod-like element 5 may be covered with Clindamycin and the head 3 covered with Vancomycin.

The possible combinations are all comprised in the present invention and may be selected depending on the needs of the patient.

In case the rod-like element 5 has a considerable extension, a wide surface from which such at least one antibiotic substance or pharmaceutical and/or therapeutic product in general spreads, involving a greater interface of the bone end to which it is connected is produced.

The head 3, the rod-like element 5 and possibly the central body 2 may be obtained in different dimensions or sizes, for example small, medium and large.

Figure 4:
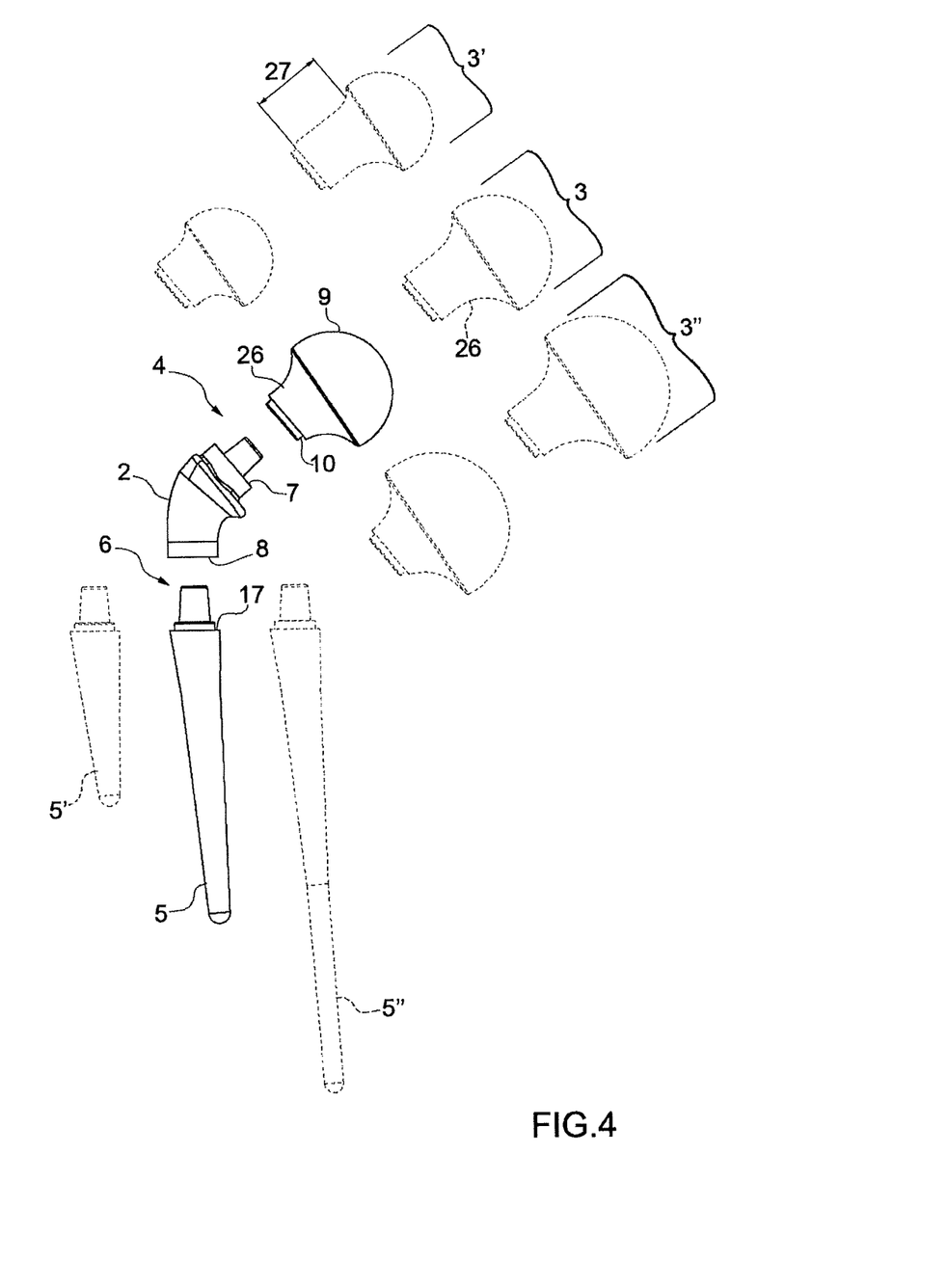
FIG. 4 is an exploded side view of the different sizes of an adjustable modular spacer device according to the invention.

With reference to the embodiment of FIG. 4, the different dimensions or sizes of the head 3 are represented with a dashed line and indicated with 3' and 3" and the different dimensions or sizes of the rod-like element 5 are indicated with 5', 5".

Further dimensions or sizes of the head 3, of the rod-like element 5 and possibly of the central body 2, with respect to those indicated previously, can be provided without departing from the scope of protection of the present invention.

Figures 5, 7:
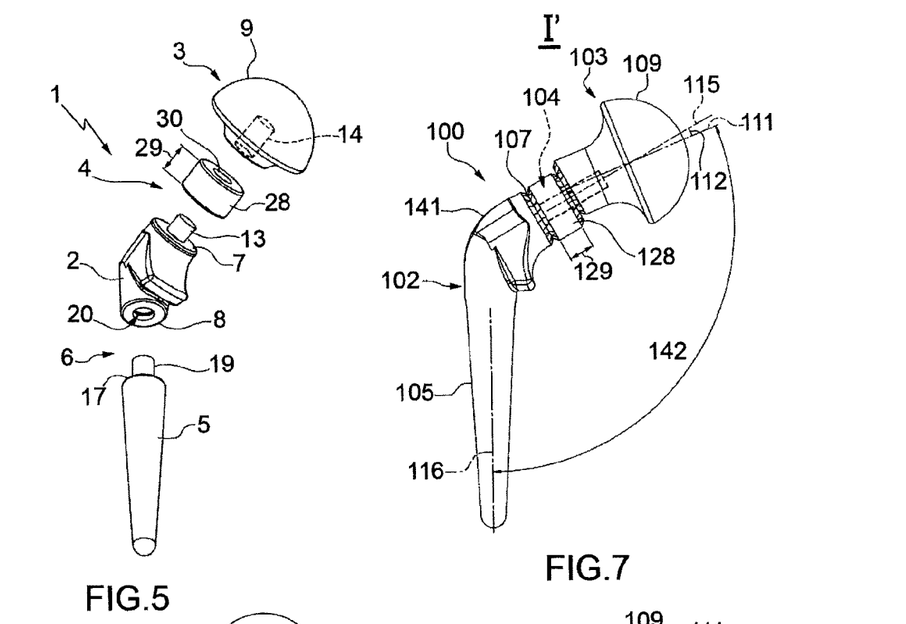
FIG. 5 is an exploded perspective view of a further embodiment of the adjustable modular spacer device of FIG. 1.
FIG. 7 is a side view of a further embodiment of the adjustable modular spacer device according to the present invention.

According to a further version of the present invention the head 3, 3', 3" can have an elongated portion 26, interposed between the cap 9 and the base 10.

The elongated portion 26 defines an offset distance 27 between the cap 9 and the base 10, thus allowing to modify the dimensions of the spacer device 1 and, in particular, the distance of the cap 9 from the central body 2.

The elongated portion 26 of the head 3, 3', 3" can be realized in different measures, according to specific needs.

The dimensions of the first connection means 4 for the different dimensions or sizes provided for the central body 2 and/or the head 3 are the same.

Therefore, the different sizes of the central body 2 and/or of the head 3 are interchangeable with respect to each other independently.

Analogously, the dimensions of the second connection means 6 for the different dimensions or sizes provided for the central body 2 and/or for the rod-like element 5 are the same. Therefore, different sizes of the central body 2 and/or of the rod-like element are interchangeable with respect to each other independently.

It is thus possible to combine any size of the central body 2 and/or of the head 3 and/or of the rod-like element 5, maintaining the functionality and the stability of the spacer device 1 upon implantation thereof in the articulation.

Actually, the spacer device 1 may be adapted and made more congruent to the different dimensions of the hip and/or shoulder articulation of each patient, even in presence of serious illnesses.

The spacer device 1 is assembled by the surgeon in the moments prior to the implantation into the seat of the articulation, selecting the size of each component according to the real needs and sizes of the patient.

Therefore, the modularity and the simplicity of the assembly of the spacer device 1 allow to easily adapt the latter to the different anthropomorphic measures of the articulation of the hip and/or of the shoulder of the patient.

In fact, the surgeon being able to choose any size combination of the central body 2 and/or of the head 3 and/or of the rod-like element 5, independent of each other, is able to realize different dimensions or sizes of the spacer device 1, according to the needs of the case and, therefore, he has not to manually modify the dimensions of the components of the spacer device 1.

Furthermore, the surgeon during the assembling of the first connection means 4 may modify the inclination of the head 3 with respect to the central body 2 along the longitudinal plane 50 and/or along the transverse plane 52, according to the methods described beforehand.

Similarly, the surgeon during the assembling of the second connection means 6 may modify the inclination of the rod-like element 5 with respect to the central body 2 along the longitudinal plane 50 and/or along the sagittal plane 51.

The times required for executing the implantation of the spacer device 1 are reduced with respect to the times required by the spacer devices of the known type.

Furthermore, in order to guarantee an extensive range of choice for the surgeon, the central body 2, the head 3 and the rod-like element 5, may be provided, separately, in special casings/containers, each containing a single size.

Figures 6, 8:
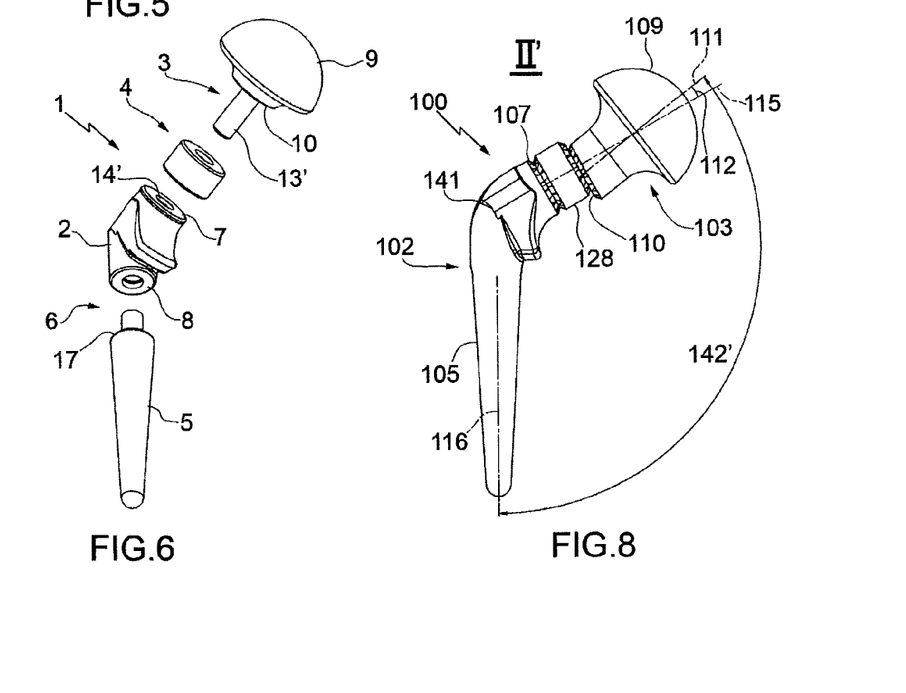
FIG. 6 is an exploded perspective view of a further embodiment of the adjustable modular spacer device according to FIG. 1.
FIG. 8 is a side view of a further configuration of assembly of the adjustable modular spacer device of FIG. 7.

According to a further embodiment of the present invention illustrated in FIG. 6, at least one annular element 28 positionable between the head 3 and the body 2 and/or between the rod-like element 5 and the central body 2 is provided.

The at least one annular element 28 defines an offset distance 29 between the head 3 and the central body 2 and/or between the rod-like element 5 and the central body 2, allowing to further modify the dimensions of the spacer device 1.

The at least one annular element 28 comprises a through central opening 30, through which the pin 13 or the pin 19 respectively of the first connection means 4 or of the second connection means 6 can be inserted.

The diameter of the through opening 30 is slightly greater than the diameter of the pins 13, 19.

Thus, it is possible to guarantee co-axiality and a correct relative positioning between the pin 13, 19 and the at least one annular element 28, thus ensuring a stable connection of the annular element 28 interposed between the central body 2 and the head 3 and/or between the central body 2 and the rod-like element 5.

Similarly to what previously disclosed about the head 3, the central body 2 and the rod-like element 5, even the at least one annular element 28 can be realized in biocompatible material.

Furthermore, the at least one annular element 28 can be provided in different dimensions or sizes, not illustrated.

A further embodiment of a spacer device 100 according to the present invention is illustrated in FIGS. 8 and 9.

Hereinafter, the elements having the same characteristics as those previously described shall be indicated with the same reference numbers increased by 100 units.

The spacer device 100 differs from the previous embodiment relatively to the configuration of the central body 102.

The spacer device 100 comprises a central body 102, provided with a rod-like element 105, integral to the central body 102, suitable to be fixedly connected at the bone end of the shoulder articulation, or at the upper humeral end, or at the bone end of the knee articulation, or at the upper femoral end, a head 103, suitable to be place within the glenoid cavity of the shoulder articulation or within the acetabular cavity of the hip articulation, and means 104 for connecting the central body 102 to the head 103.

Consequently, in the spacer device 100 second connection means previously disclosed are not present.

The central body 102 and the head 103 are assembled together to make up the spacer device 100 according to the present invention.

The spacer device 100 differs from the previous embodiment due to the presence of a central body 102 comprising a rod-like element 105, substantially frusto-conical shaped, radiused to a connection portion 141.

The rod-like element 105 has a longitudinal axis 116. The central body 102, at one end of the connection portion 141, opposite to the rod-like element 105, has a substantially flat surface 107, suitable to be abutted against the head 103.

The head 103 has, at one end, a spherical or a semi spherical or a similar shape cap 109, suitable to be placed within the glenoid or acetabular articular cavity, and at the opposite end a base 110.

The spherical cap 109, that is radiused to the base 110, has a central symmetry axis 111.

Analogously to the previous embodiment, the base 110 can be perpendicular or inclined to the central symmetry axis 111 by an angle 112, causing different configurations of assembly of the spacer device 100. The first connection means 104 comprise a pin 113 and a seat 114, connectable together according to previously described methods, along an axis 115.

According to an embodiment of the spacer device 100, the pin 113 projects from the central body 102, while the seat 114 is obtained in the head 103, at the second base 110.

According to a further embodiment, not illustrated, the position of the pin 113 and that of the seat 114 can be inverted each other.

The inclination of the base 110 with respect to the central symmetry axis 111 allows to obtain different configurations of assembly of the spacer device 100, and in particular to obtain different relative positioning of the head 103 with respect to the central body 102 according to disclosed way with reference to the previous embodiment.

Therefore, during the assembling of the spacer device 100, by turning the head 103 around the axis 115, a precession motion of the cap 109 around the axis 115 is determined, varying the inclination of the head 3 with respect to the central body 102.

In particular, it is possible to modify the inclination of the central symmetry axis 111 of the cap 109 with respect to the longitudinal plane 50 and/or to the transverse plane 52.

By way of a non-limiting example, in FIGS. 7 and 8 with reference I' and II', two possible configurations of assembly of the spacer device 100, the latter laying on the longitudinal plane 50, are illustrated.

With reference to the configuration of assembly I' illustrated in FIG. 7, the central symmetry axis 111 of the head 103 is inclined with respect to the longitudinal axis 116 of the rod-like element 105 by an angle 142.

By way of an example, the inclination angle 142 has a width comprised between 80° and 120°.

Preferably, such width is comprised between 90° and 110°.

The second configuration of assembly II' is reached by turning the head 103 of about 180° around the axis 115 of the first connection means 104.

In the second configuration of assembly II' the central symmetry axis 109 of the head 103 is inclined with respect to the longitudinal axis 116 by an angle 142'.

In particular, the angle 142' is greater than the angle 142.

In a version of the spacer device 100, the angle 142', indeed, can have a width comprised between 125° and 150°.

Preferably, such width is comprised between 125° and 135°.

However, it is possible to obtain a substantially infinite number of configurations of assembly of the spacer device 100, according to the amount of the rotation of the head 103 around the central body 102. In order to allow the surgeon to obtain the desired assembly configuration, reference notches 140 can be provided on the head 103, at the base 110, and/or on the central body 102, at the end 107.

As illustrated in FIGS. 7 and 8, the device 100 can comprise at least one annular element 128 interposed between the head 103 and the central body 102.

Similarly to the previous embodiment, the at least one annular element 128 defines an offset distance 129 between the head 103 and the central body 102.

The body 102, the head 103 and possibly the at least one annular element 128 can be provided in different dimensions or sizes, not illustrated.

Since the connection means 104 for any dimension or size of the head 103 and of the central body 102 have the same dimensions, it is possible to combine any size of the head 103 and of the central body 102 maintaining the functionality and the stability of the spacer device 100.

The spacer device 100 has a simplified structure than that of the previous embodiment.

The central body 102, indeed, comprises a rod-like element 105 that is integral to a connection portion 141. Therefore the spacer device 100 lacks of second connection means.

Even if the spacer device 100 has a lower modularity than the previous embodiment, however it allows to obtain a substantially infinite of number configurations of assembly, with reference to the sizes of the head 103 and of the central body 102 that can be associated to each other and to the possibility of modify the inclination of the head 103 with respect to the central body 102.

The spacer device 1, 100 being provided in several parts, which can be assembled with respect to each other, may be easily adapted to the dimensions of the articular glenoid or acetabular seat in which it should be implanted, obtaining a high congruency of the dimension thereof with the articular seat.

This allows for guaranteeing a high efficiency of the spacer device 1, 100 which leads to a high mobility of the articulation in which it is implanted and a good quality of life of the patient over the period required for rehabilitation.

Therefore, the spacer device of the present invention allows the surgeon to choose the best geometries and dimensions of the spacer for easily adapting it to the actual articular dimensions of the patient, assessed following the removal of the infected prosthesis.

Moreover, it is possible to variously combine pharmaceutical and/or therapeutic products integrated or to be applied to the components of the spacer device 1, 100 depending on the type of infection intended to be treated.

The invention thus conceived can be subjected to numerous modifications and variants all falling within the inventive concept of the present invention.

Finally, the surfaces that abut against each other can have complementary geometries, as for example stepped configurations that insert in corresponding edges or perimeters positioned on the opposite surface, or other means suitable to guarantee the better coupling stability of the same, together with an increase of the stability of the implant itself.

Furthermore, these geometries or means, may also serve to create a substantial insulation of the connecting means with respect to the surrounding tissues, so as to avoid as much as possible the infiltration of bacteria inside the device or to prevent that any non-compatible materials, that are present in said areas, can come into contact with the tissue area surrounding the implant itself.

Furthermore, all details can be replaced by other technically equivalent elements. In practice, the materials used, as well as the shapes and contingent dimensions, may vary, depending on the requirements, without departing from the scope of protection of the claims that follow.

Furthermore, the characteristics described in a particular version or embodiment can be replaced by other characteristics of other versions or embodiment, without departing from the scope of protection of the present invention.

The invention claimed is:

1. Adjustable modular spacer device for the treatment of an articulation of the human body, comprising:
a connecting central body, wherein said central body is provided with an end having a substantially flat first surface;
a head, adapted to be arranged within an articular cavity, said head comprising a cap and a base opposite to said cap;
wherein said cap and said base are connected by a radiused portion having a concave surface,
wherein said cap has a central symmetry axis;
a rod-like element, adapted to be fixedly connected at a bone end;
a first means for connecting said head to said central body;
wherein said first connection means are adjustable and adapted to adjust the inclination of the head with respect to said central body along a longitudinal plane and/or along a transverse plane of the human body,
wherein said first connection means comprise a pin and a seat complementary to each other, defining a first longitudinal axis of coupling of said head with said central body,
wherein said central symmetry axis is inclined with respect to said first axis of said first connections means by an angle and said central body, which acts as a connecting element between said head and said rod-like element,
wherein said pin projects from said first surface of said central body and said seat is provided in said base of said head or wherein said pin projects from said base of said head and said seat is provided in said first surface of said central body.

2. Adjustable modular spacer device according to claim 1, wherein said angle is comprised between 5° and 20°.

3. Adjustable modular spacer device according to claim 1, wherein said central body has said substantially "elbow" shape with two ends opposite to each other,
wherein said ends respectively have said first surface and a second surface,
wherein said first surface and said second surface are substantially plane.

4. Adjustable modular spacer device according to claim 1, comprising second means for connecting said central body to said rod-like element, adjustable and adapted for adjusting the inclination of said rod-like element with respect to said central body along said longitudinal plane and/or along said sagittal plane of the human body.

5. Adjustable modular spacer device according to claim 4, wherein said second connection means comprise a pin and a seat complementary with respect to each other, defining a second longitudinal coupling axis of said rod-like element with said central body.

6. Adjustable modular spacer device according to claim 5, wherein said pin projects upwards from said rod-like element and said seat is provided in second surface of said central body.

7. Adjustable modular spacer device according to claim 5, wherein said pin projects from said second surface of said central body and said seat is provided in said rod-like element.

8. Adjustable modular spacer device according to claim 5, wherein said rod-like element has a longitudinal axis inclined with respect to said second axis by an angle.

9. Adjustable modular spacer device according to claim 8, wherein said angle is comprised between 3° and 20°.

10. Adjustable modular spacer device according to claim 1, further comprising at least one annular element interposed between said central body and said head and/or between said central body and said rod-like element.

11. Adjustable modular spacer device according to claim 10, wherein at least one among said central body, said rod-like element, said head, and said at least one annular element has a set of sizes.

12. Adjustable modular spacer device according to claim 10, wherein said first connection means are conformed in order to allow the assembly of any size of said head, said central body, or said at least one annular element.

13. Adjustable modular spacer device according to claim 10, further comprising a second means for connecting said central body to said rod-like element, adjustable and adapted for adjusting the inclination of said rod-like element with respect to said central body along said longitudinal plane and/or along said sagittal plane of the human body,
wherein said second connection means are conformed in order to allow the assembly of any size of said rod-like element and/or of said central body and/or, possibly, of said at least one annular element.

14. Adjustable modular spacer device according to claim 10, wherein at least one among said central body, said head, said rod-like element, and said at least one annular element comprises at least one pharmaceutical and/or therapeutic product comprising an antibiotic substance, an anti-infective drug, or a combination thereof.

15. Adjustable modular spacer device according to claim 14, wherein the antibiotic substance is selected from the group consisting of Gentamicin, Vancomycin, Clindamycin, or a combination thereof.

16. Adjustable modular spacer device according to claim 1, wherein said central symmetry axis of said cap is inclined with respect to said longitudinal axis of said rod-like element by an inclination angle that is variable and comprised between 100° and 160° or between 80° and 120° or between 125° and 150°.

17. Adjustable modular spacer device according to claim 1, wherein said central symmetry axis of said cap is inclined with respect to said longitudinal axis of said rod-like element by an inclination angle that is variable and comprised between 110° and 150° or between 90° and 110° or between 125° and 135°.

18. Adjustable modular spacer device according to claim 1, wherein the concave surface is an external surface of the device.

19. An adjustable modular spacer device for the treatment of an articulation of the human body, comprising:
a connecting central body, wherein said central body is provided with an end having a substantially flat first surface;
a head, adapted to be arranged within an articular cavity, said head comprising a cap and a base opposite to said cap,
wherein said cap and said base are connected by an elongated portion having a concave cross section,
wherein said cap has a central symmetry axis;
a rod-like element, adapted to be fixedly connected at a bone end;
a first means for connecting said head to said central body, wherein said first connection means are adjustable and adapted to adjust the inclination of the head with respect to said central body along a longitudinal plane and/or along a transverse plane of the human body,
wherein said first connection means comprise a pin and a seat complementary to each other, defining a first longitudinal axis of coupling of said head with said central body,
wherein said central symmetry axis is inclined with respect to said first axis of said first connections means by an angle and said central body, which acts as a connecting element between said head and said rod-like element.

* * * * *